US00PP36919P2

(12) United States Plant Patent
Tomomatsu

(10) Patent No.: US PP36,919 P2
(45) Date of Patent: Sep. 2, 2025

(54) ***CATHARANTHUS* PLANT NAMED 'Suncath 783'**

(50) Latin Name: *Catharanthus roseus*
Varietal Denomination: Suncath 783

(71) Applicant: Koichi Tomomatsu, Shiga (JP)

(72) Inventor: Koichi Tomomatsu, Shiga (JP)

(73) Assignee: SUNTORY FLOWERS LIMITED, Tokyo (JP)

( * ) Notice: Subject to any disclaimer, the term of this patent is extended or adjusted under 35 U.S.C. 154(b) by 0 days.

(21) Appl. No.: 18/896,774

(22) Filed: Sep. 25, 2024

(51) Int. Cl.
*A01H 5/02* (2018.01)
*A01H 6/08* (2018.01)

(52) U.S. Cl.
USPC ..... Plt./263.1

(58) Field of Classification Search
USPC ..... Plt./263.1
See application file for complete search history.

*Primary Examiner* — Susan McCormick Ewoldt
(74) *Attorney, Agent, or Firm* — C. Anne Whealy

(57) ABSTRACT

A new and distinct cultivar of *Catharanthus* plant named 'Suncath 783', characterized by its upright to outwardly spreading and uniformly mounding plant habit; vigorous growth habit; freely basal and lateral branching habit; freely flowering habit; long flowering period; double-type flowers with purplish pink-colored petals and petaloids; and good garden performance.

2 Drawing Sheets

Figure 1:
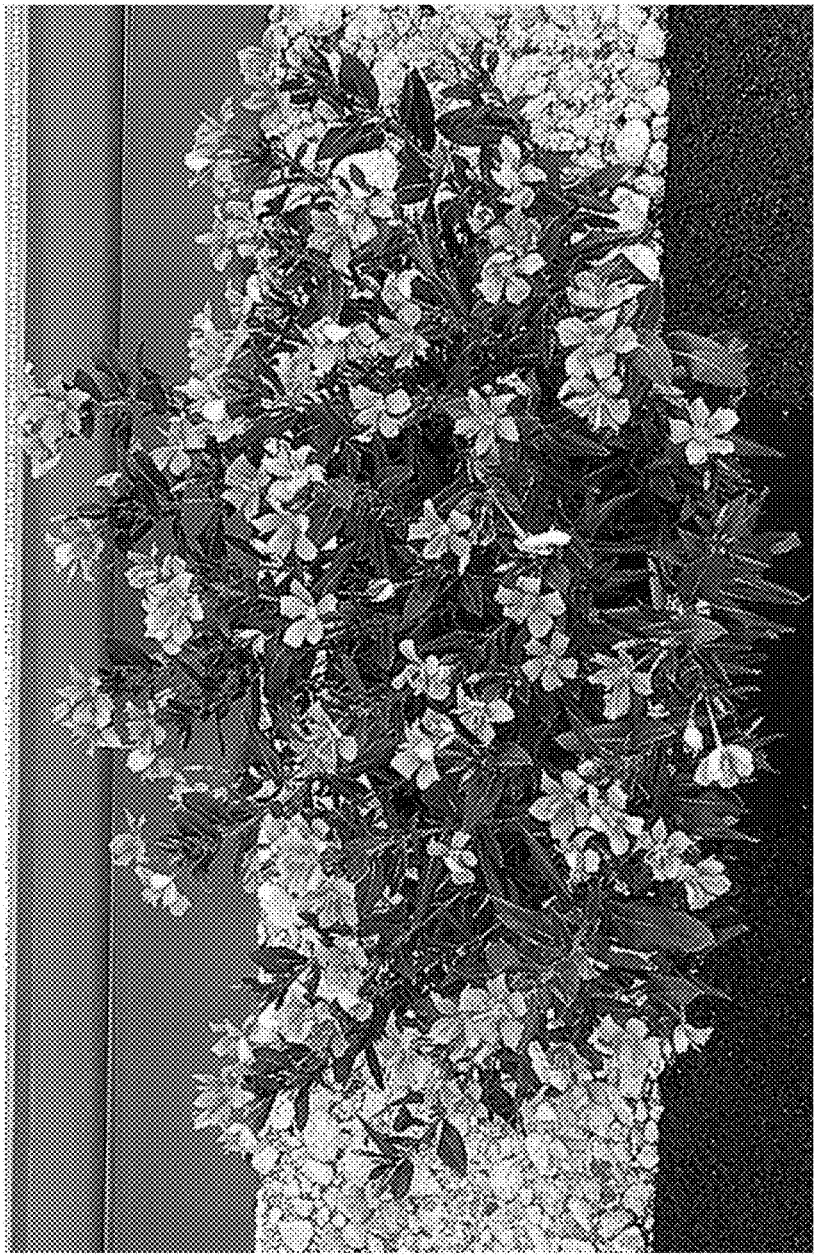

Botanical designation: *Catharanthus roseus.*
Cultivar denomination: 'SUNCATH 783'.

BACKGROUND OF THE INVENTION

The present invention relates to a new and distinct *Catharanthus* plant, botanically known as *Catharanthus roseus*, commonly referred to periwinkle and hereinafter referred to by the cultivar name 'Suncath 783'.

The new *Catharanthus* plant is a product of a planned breeding program conducted by the Inventor in Higashiomi, Shiga, Japan. The objective of the breeding program is to develop new upright and freely branching *Catharanthus* plants with numerous attractive flowers.

The new *Catharanthus* plant originated from an open-pollination in Higashiomi, Shiga, Japan in October, 2018 of a proprietary selection of *Catharanthus roseus* identified as code designation V18-35-2, not patented, as the female, or seed, parent with an unknown proprietary selection of *Catharanthus roseus* as the male, or pollen, parent. The new *Catharanthus* plant was discovered and selected by the Inventor as a single flowering plant from within the progeny of the stated open-pollination in a controlled greenhouse environment in Higashiomi, Shiga, Japan in March, 2019.

Asexual reproduction of the new *Catharanthus* plant by vegetative tip cuttings in a controlled greenhouse environment in Higashiomi, Shiga, Japan since December, 2019, has shown that the unique features of this new *Catharanthus* plant are stable and reproduced true to type in successive generations.

SUMMARY OF THE INVENTION

Plants of the new *Catharanthus* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Suncath 783'. These characteristics in combination distinguish 'Suncath 783' as a new and distinct *Catharanthus* plant:

1. Upright to outwardly spreading and uniformly mounding plant habit.
2. Vigorous growth habit.
3. Freely basal and lateral branching habit.
4. Freely flowering habit.
5. Long flowering period.
6. Double-type flowers with purplish pink-colored petals and petaloids.
7. Good garden performance.

Plants of the new *Catharanthus* can be compared to plants of the female parent selection. Plants of the new *Catharanthus* differ primarily from plants of the female parent selection in flower type as plants of the new *Catharanthus* have double-type flowers whereas plants of the female parent selection have single-type flowers. In addition, flower petals and petaloids of plants of the new *Catharanthus* are lighter purplish pink in color than flower petals of plants of the female parent selection.

Plants of the new *Catharanthus* can be compared to plants of the *Catharanthus roseus* 'Suncatha 2335', disclosed in U.S. Plant Pat. No. 28,153. In side-by-side comparisons, plants of the new *Catharanthus* differ from plants of 'Suncatha 2335' in the following characteristics:

1. Plants of the new *Catharanthus* are taller and broader than plants of 'Suncatha 2335'.
2. Plants of the new *Catharanthus* are more freely branching than plants of 'Suncatha 2335'.
3. Plants of the new *Catharanthus* have smaller and flatter leaves than plants of 'Suncatha 2335'.
4. Plants of the new *Catharanthus* are more freely flowering than plants of 'Suncatha 2335'.

5. Plants of the new *Catharanthus* have smaller flowers than plants of 'Suncatha 2335'.
6. Plants of the new *Catharanthus* and 'Suncatha 2335' differ in flower color as plants of the new *Catharanthus* have purplish pink-colored petals and petaloids whereas plants of 'Suncatha 2335' have bright reddish purple-colored petals and petaloids.

BRIEF DESCRIPTION OF THE PHOTOGRAPHS

The accompanying colored photographs illustrate the overall appearance of the new *Catharanthus* plant showing the colors as true as it is reasonably possible to obtain in colored reproductions of this type. Colors in the photographs may differ slightly from the color values cited in the detailed botanical description which accurately describe the colors of the new *Catharanthus* plant.

The photograph on the first sheet (FIG. 1) is a side perspective view of a typical flowering plant of 'Suncath 783' grown in a container.

Figure 2:
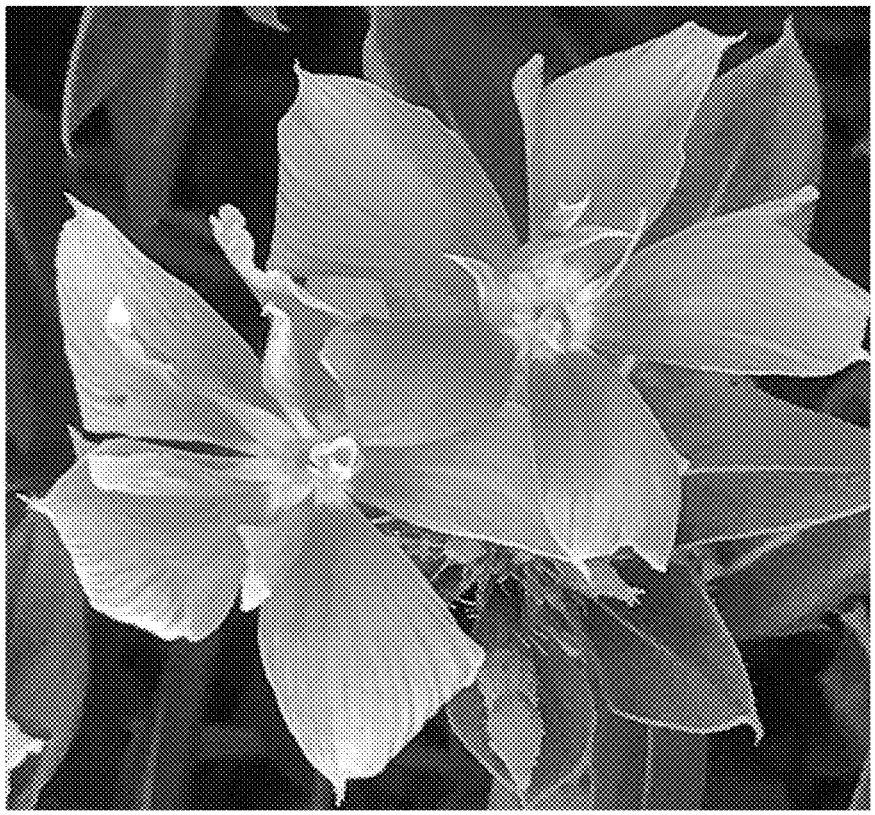

The photograph on the second sheet (FIG. 2) is a close-up view of a typical flowering plant of 'Suncath 783'.

DETAILED BOTANICAL DESCRIPTION

The aforementioned photographs and following observations, measurements and values describe plants grown during the summer in 24-cm containers in an outdoor nursery in Higashiomi, Shiga, Japan and under cultural practices typical of commercial production. During the production of the plants, day temperatures averaged 25° C. and night temperatures averaged 15° C. Plants were four months old when the photographs and the description were taken. In the following description, color references are made to The Royal Horticultural Society Colour Chart, 2015 Edition, except where general terms of ordinary dictionary significance are used.

Botanical classification: *Catharanthus roseus* 'Suncath 783'.

Parentage:

*Female, or seed, parent*.—Proprietary selection of *Catharanthus roseus* identified as code designation V18-35-2, not patented.

*Male, or pollen, parent*.—Unknown proprietary selection of *Catharanthus roseus*, not patented.

Propagation:

*Type*.—By vegetative tip cuttings.

*Time to initiate roots, summer*.—About two weeks at temperatures about 30° C.

*Time to initiate roots, winter*.—About three weeks at temperatures about 25° C.

*Time to produce a rooted young plant, summer*.—About five weeks at temperatures about 30° C.

*Time to produce a rooted young plant, winter*.—About six weeks at temperatures about 25° C.

*Root description*.—Fibrous; typically white in color, actual color of the roots is dependent on substrate composition, water quality, fertilizer type and formulation, substrate temperature and physiological age of roots.

*Rooting habit*.—Freely branching; medium density.

Plant description:

*Plant and growth habit*.—Upright to outwardly spreading and uniformly mounding plant habit; freely basal and lateral branching habit, about six basal branches each with about 13 secondary branches developing per plant; pinching is typically not required; vigorous growth habit.

*Plant height*.—About 31 cm.

*Plant diameter*.—About 51 cm.

Lateral branch description:

*Length*.—About 25.8 cm.

*Diameter*.—About 1.8 mm.

*Internode length*.—About 1.8 cm.

*Strength*.—Strong.

*Aspect*.—Mostly upright to outwardly spreading.

*Texture*.—Smooth, glabrous.

*Color*.—Close to 145C.

Leaf description:

*Arrangement*.—Opposite, simple.

*Length*.—About 4.4 cm.

*Width*.—About 1.8 cm.

*Shape*.—Elliptic.

*Apex*.—Acute.

*Base*.—Obtuse.

*Margin*.—Entire, undulate.

*Texture, upper and lower surfaces*.—Smooth, glabrous.

*Venation pattern*.—Pinnate; reticulate.

*Color*.—Developing leaves, upper surface: Close to 137A. Developing leaves, lower surface: Close to 138B. Fully expanded leaves, upper surface: Close to 138A; venation, close to 144C. Fully expanded leaves, lower surface: Close to 144A; venation, close to 144D.

*Petioles*.—Length: About 4.8 mm. Diameter: About 1.2 mm. Texture, upper and lower surfaces: Sparsely pubescent. Color, upper and lower surfaces: Close to 144D.

Flower description:

*Flower arrangement and habit*.—Double-type star-shaped salverform flowers arising from upper leaf axils; freely flowering habit with about three flowers per lateral branch and about 126 flowers per plant during the flowering season; flowers face mostly upright to outwardly.

*Fragrance*.—None detected.

*Flowering habit*.—Plants begin flowering about two to three weeks after planting; long flowering period, in the garden, plants flower continuously from the early summer to late autumn in Japan.

*Flower longevity*.—Individual flowers last about two to three days on the plant; flowers not persistent.

*Flower buds*.—Length: About 3.5 cm. Diameter: About 3.9 mm. Shape: Ovoid to cylindrical. Color: Distally, close to 62C, and towards the base, close to 144D.

*Flower diameter*.—About 3.1 cm.

*Flower length (depth)*.—About 3.7 cm.

*Tube length*.—About 2.3 cm.

*Tube diameter, proximally*.—About 1.5 mm.

*Tube diameter, distally*.—About 2.4 mm.

*Corolla*.—Arrangement: Five petals in a single whorl and five petaloids in an inner whorl (also referred to as a paracorolla); petals and petaloids fused at the base into a tube. Petal length from throat: About 1.6 cm. Petal width: About 1.1 cm. Petal eye zone diameter: About 3.9 mm. Petal shape: Broadly obovate to transversely elliptic. Petal apex: Cuspidate. Petal base: Fused to corolla tube. Petal margin: Entire to incised; slightly undulate. Petal texture, upper and lower surfaces: Smooth, glabrous. Throat texture: Smooth, glabrous. Tube texture: Smooth, glabrous. Color: Petal, when opening, upper surface: Close to 68A. Petal, when opening, lower surface: Close to 68B. Petal, fully opened, upper surface: Close to 68A and 68B; distally, color fading to almost white with development; eye zone, close to 8D. Petal, fully opened, lower surface: Close to 69C. Throat: Distally, close to 144A, and proximally, close to 144C. Tube: Distally, close to 144B, and proximally, close to N144D. Petaloid length from throat: About 1.4 cm. Petaloid width: About 2.9 mm. Petaloid shape: Linear. Petaloid apex: Sharply acute. Petaloid base: Fused. Petaloid margin: Entire; undulate. Petaloid texture, upper and lower surfaces: Smooth, glabrous. Color: Petaloid, when opening and fully opened, upper surface: Close to 68A; distally, color fading to white with development. Petaloid, when opening and fully opened, lower surface: Close to 69B.

*Calyx*.—Arrangement: Star-shaped tubular calyx with five sepals fused towards the base and curled outwardly. Sepal length: About 3.4 mm. Sepal width: About 1.1 mm. Sepal shape: Lanceolate. Sepal apex: Acuminate. Sepal margin: Entire. Sepal texture, upper and lower surfaces: Sparsely pubescent. Color, upper and lower surfaces: Close to 144B.

*Peduncles*.—Length: About 2.3 mm. Diameter: About 1.2 mm. Angle: Upright to outwardly. Strength: Strong. Texture: Smooth, glabrous. Color: Close to 144C.

*Reproductive organs*.—Stamens: Quantity per flower: Five; filaments fused to the corolla tube. Anther size: About 1 mm by 1.4 mm. Anther shape: Narrowly elliptic. Anther color: Close to 8C. Pollen amount: Sparse. Pollen color: Close to 8D. Pistils: Quantity per flower: One. Pistil length: About 2.2 cm. Style color: Close to 145B. Stigma shape: Globose. Stigma color: Close to 145A. Ovary color: Close to 145A. Seeds and fruits: To date, seed and fruit development have not been observed on plants of the new *Catharanthus*.

Garden performance: Plants of the new *Catharanthus* have been observed to have good garden performance and to tolerate wind, rain and temperatures ranging from about 5° C. to about 35° C. to 40° C.

Pathogen & pest resistance: To date, plants of the new *Catharanthus* have not been observed to be resistant to pathogens and pests common to *Catharanthus* plants.

It is claimed:

1. A new and distinct *Catharanthus* plant named 'Suncath 783' as herein illustrated and described.

* * * * *